(12) United States Patent
Eilers et al.

(10) Patent No.: US 10,787,415 B2
(45) Date of Patent: *Sep. 29, 2020

(54) DMF DISTILLATION

(71) Applicant: Tate & Lyle Technology Limited, London (GB)

(72) Inventors: Thomas Eilers, Cary, IL (US); David A. Dentel, Spanish Fort, AL (US); Halil Aktas, NB Zaandam (NL)

(73) Assignee: Tate & Lyle Technology Limited, London (GB)

( * ) Notice: Subject to any disclaimer, the term of this patent is extended or adjusted under 35 U.S.C. 154(b) by 4 days.

This patent is subject to a terminal disclaimer.

(21) Appl. No.: 16/207,426

(22) Filed: Dec. 3, 2018

(65) Prior Publication Data

US 2019/0100488 A1    Apr. 4, 2019

Related U.S. Application Data

(63) Continuation of application No. 15/071,655, filed on Mar. 16, 2016, now Pat. No. 10,179,760.

(60) Provisional application No. 62/134,299, filed on Mar. 17, 2015.

(51) Int. Cl.
| | | |
|---|---|---|
| *C07C 231/24* | (2006.01) | |
| *C07C 233/03* | (2006.01) | |
| *B01D 3/10* | (2006.01) | |
| *B01D 3/14* | (2006.01) | |
| *B01D 3/42* | (2006.01) | |

(52) U.S. Cl.
CPC .............. *C07C 231/24* (2013.01); *B01D 3/10* (2013.01); *B01D 3/143* (2013.01); *B01D 3/4205* (2013.01)

(58) Field of Classification Search
CPC ..... C07C 231/24; C07C 233/03; B01D 3/143; B01D 3/10; B01D 3/4205
USPC ..................................... 536/123.13
See application file for complete search history.

(56) References Cited

U.S. PATENT DOCUMENTS

| | | | |
|---|---|---|---|
| 4,385,965 A | 5/1983 | Müller et al. | |
| 10,179,760 B2 * | 1/2019 | Eilers | .................... C07C 231/24 |
| 2012/0077972 A1 | 3/2012 | Boutzale et al. | |

FOREIGN PATENT DOCUMENTS

| | | |
|---|---|---|
| WO | 2012071385 A1 | 5/2012 |
| WO | 2013056128 A1 | 4/2013 |

OTHER PUBLICATIONS

Office Action for U.S. Appl. No. 15/071,655 dated Dec. 1, 2017 (15 pages).
Final Office Action for U.S. Appl. No. 15/071,655 dated Apr. 27, 2018 (13 pages).
Notice of Allowance for U.S. Appl. No. 15/071,655 dated Sep. 6, 2018 (13 pages).

* cited by examiner

*Primary Examiner* — Yih-Horng Shiao
(74) *Attorney, Agent, or Firm* — RatnerPrestia

(57) ABSTRACT

A method of obtaining purified DMF from a mixture comprising DMF and hydrogen chloride (HCl) involving distillation is provided.

26 Claims, 1 Drawing Sheet

DMF DISTILLATION

CROSS-REFERENCE TO RELATED APPLICATION

This application is a continuation of U.S. application Ser. No. 15/071,655, filed Mar. 16, 2016, which claims priority from U.S. Provisional Application No. 62/134,299, filed Mar. 17, 2015, the entire disclosure of which is incorporated herein by reference in its entirety for all purposes.

TECHNICAL FIELD

The present invention relates to a method of purifying dimethylformamide (DMF). In particular, the present invention relates to a method of obtaining purified DMF from a mixture comprising DMF and hydrogen chloride (HCl).

BACKGROUND

Although the present invention is illustrated herein in relation to the synthesis of sucralose, the method disclosed can be applied to any situation where it is desirable to obtain purified DMF from a mixture containing DMF and HCl.

Methods for producing sucralose intermediates and sucralose from a stream comprising a sucrose-6-acylate in a reaction vehicle are known. For example, EP 0409549 discloses a process for the chlorination of a sucrose-6-acylate in a tertiary amide reaction vehicle to produce a sucralose-6-acylate, such as sucralose-6-acetate. A large excess of an acid chloride, such as phosgene, is used as the chlorination agent in this process. Following the chlorination reaction, the excess chlorinating agent is quenched using a suitable base, thereby forming the chloride salt of the base. The resulting product stream thus comprises a sucralose-6-acylate, the tertiary amide reaction vehicle, water, and salts.

Methods for preparing sucrose-6-acylate starting materials for chlorination to sucralose-6-acylate are known, for example, in U.S. Pat. Nos. 4,950,746; 4,889,928; 5,023,329; 5,089,608; 5,034,551; 5,470,969; 5,440,026; 6,939,962; and US 2007-0227897.

Other methods of chlorinating sucrose-6-acylate to give sucralose-6-acylate are known, for example, in U.S. Pat. No. 4,380,476; US 2006-0205936; U.S. Pat. No. 7,932,380; and US 2007-0100139.

It is often desirable to recover the reaction solvent after completion of a reaction to minimise waste, or to reuse the solvent. Particularly in sucralose synthesis, it is desirable to recover DMF from the reaction mixture after chlorination of a sucrose-6-acylate to a sucralose-6-acylate for reuse.

U.S. Pat. No. 5,530,106 discloses a method of removing DMF from the product mixture after quench of the chlorination reaction of a sucrose-6-acylate to a sucralose-6-acylate. The process comprises removing the DMF by steam distillation.

U.S. Pat. No. 8,530,643 discloses a method of removing DMF from the reaction mixture in the chlorination of a sucrose-6-acylate to a sucralose-6-acylate, before quench of the reaction, by distillation, to afford DMF. This DMF is contaminated with HCl. According to U.S. Pat. No. 8,530,643, the HCl may be removed by treating the HCl-contaminated DMF with a base. The mixture may be treated with aqueous solutions of base, such as sodium hydroxide or sodium carbonate. Alternatively, the mixture may be treated with bases under dry conditions to keep water levels low by using sodium carbonate, calcium hydroxide, sodium hydroxide or ammonia.

Accordingly, there is a need for methods of obtaining purified DMF from mixtures of DMF and HCl.

SUMMARY

According to a first aspect of the present invention, there is provided:
1) a method of producing purified dimethylformamide from a feed mixture comprising dimethylformamide and hydrogen chloride, comprising:
   distilling the feed mixture to afford a more volatile fraction and a less volatile fraction, wherein the more volatile fraction has a lower hydrogen chloride content than the less volatile fraction, and
   collecting the more volatile fraction to afford a collected more volatile fraction, at least a portion of which affords a purified dimethylformamide product that is lower in hydrogen chloride content than the feed mixture.

There is further provided:
2) a method according to 1), wherein the distillation is carried out in a distillation column;
3) a method according to 2), wherein the distillation column comprises an upper rectifying section and a lower stripping section;
4) a method according to 3), wherein the feed mixture is introduced to the distillation column between the rectifying and stripping sections thereof;
5) a method according to any of 1) to 5), wherein a portion of the collected more volatile fraction is returned to the distillation column as a reflux stream;
6) a method according to 5), wherein the reflux stream is introduced to the distillation column at a point above the point at which the feed mixture is introduced to the distillation column;
7) a method according to 5) or 6), wherein the reflux stream is introduced to the distillation column at the top of the rectifying section;
8) a method according to any of 5) to 7), wherein the ratio of the amount of the collected more volatile fraction returned as a reflux stream to the amount of the collected more volatile fraction taken forward as purified dimethylformamide product is from 0.1:1 to 4:1 (w/w);
9) a method according to 8), wherein the ratio of the amount of the collected more volatile fraction returned as a reflux stream to the amount of the collected more volatile fraction taken forward as purified dimethylformamide product is from 0.2:1 to 1.5:1 (w/w);
10) a method according to any of 1) to 9), wherein the feed mixture is derived from a reaction mixture comprising dimethylformamide, hydrogen chloride, and reactants, reaction products, or a mixture of reactants and reaction products;
11) a method according to 10), wherein the feed mixture is distilled from the reaction mixture according to 10), to afford the feed mixture and a reaction mixture bottoms stream;
12) a method according to 10) or 11), wherein the reaction mixture is non-aqueous;
13) a method according to any of 10) to 12), wherein the reaction mixture is unquenched;
14) a method according to 13), wherein the less volatile fraction is collected and mixed with the reaction mixture bottoms stream, and the mixture produced is added to a vessel and a base is simultaneously added to the vessel to quench the reaction mixture and neutralise hydrogen chloride.

15) a method according to any of 10) to 14), wherein the reaction mixture is derived from a chlorination reaction of a sucrose-6-acylate to afford a sucralose-6-acylate;

16) a method according to any of 1) to 13) or 15), wherein the less volatile fraction is collected and treated with a base to remove hydrogen chloride;

17) a method according to any of 2) to 16), wherein the pressure in the distillation column is from 1 mbar to 1014 mbar;

18) a method according to 17), wherein the pressure in the distillation column is from 1 mbar to 100 mbar;

19) a method according to any of 2) to 18), wherein the temperature in the distillation column is from 0° C. to 150° C.;

20) a method according to 19), wherein the temperature in the distillation column is from 10° C. to 85° C.;

21) a method according to any of 1) to 20), wherein the chloride content of the purified dimethylformamide is from 0 to 1000 ppm;

22) a method according to any of 1) to 21), wherein the chloride content of the feed mixture is from 0.1% to 10% (w/w);

23) a method according to any of 10) to 22), wherein the reaction mixture is distilled to afford the feed mixture under a pressure of from 1 mbar to 300 mbar;

24) a method according to any of 10) to 23), wherein the reaction mixture is distilled to afford the feed mixture at a temperature of from 40° C. to 150° C.

25) a method according to 15), which further comprises the step of converting at least a portion of said sucralose-6-acylate to sucralose.

26) a method according to 25), which further comprises the step of isolating and purifying sucralose.

There is also provided sucralose prepared by a method disclosed herein.

Further features and advantages of the invention will become apparent from the following description of preferred embodiments of the invention, given by way of example only, which is made with reference to the accompanying drawings.

DETAILED DESCRIPTION

Figure 1:
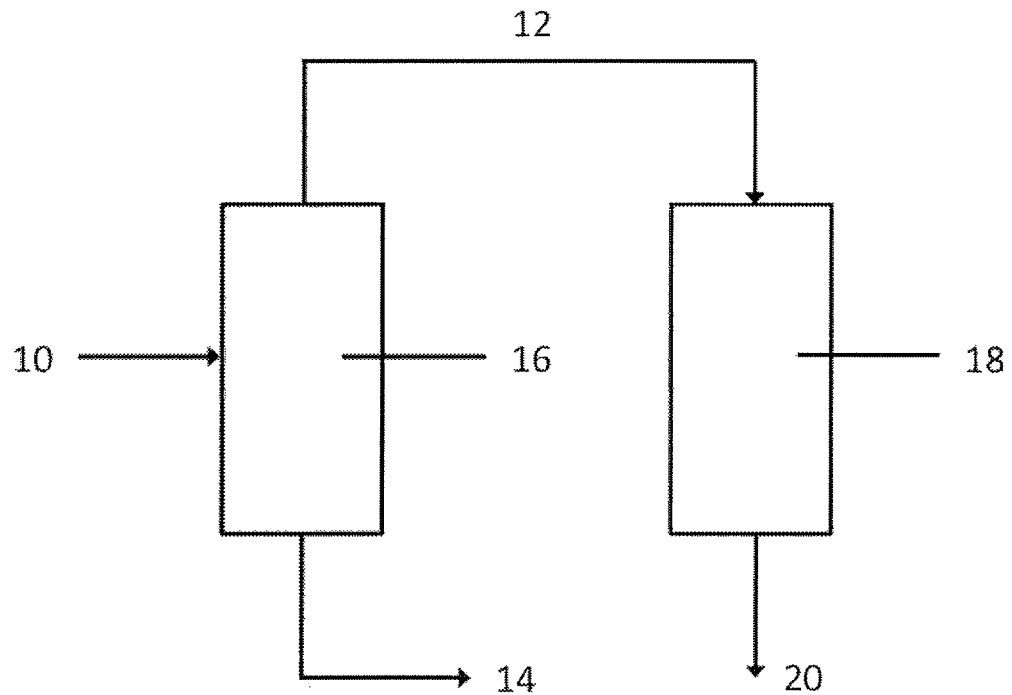
FIG. 1 is a flow diagram which shows a method for the preparation of the feed mixture containing DMF and HCl used in the invention.

Unless otherwise specified, in the specification and claims, all percentages are percentages by weight and all temperatures are in degrees Centigrade (degrees Celsius). Reduced pressure refers to a pressure less than atmospheric pressure. Temperature refers to the temperature within the vessel, unless otherwise stated. DMF refers to N,N-dimethylformamide, and HCl refers to hydrogen chloride. Sucrose-6-acylate refers to sucrose esterified at the 6-position with an acylate group that serves to protect the 6-hydroxy group during a chlorination reaction. It is preferably an aliphatic or carbocyclic aromatic acylate, more preferably a benzoate or acetate, and most preferably an acetate. A 4,1',6'-trichloro-4,1',6'-trideoxy-galactosucrose-6-acylate can also be referred to as a sucralose-6-acylate, so that 4,1',6'-trichloro-4,1',6'-trideoxy-galactosucrose-6-acetate can also be referred to as sucralose-6-acetate. Both terminologies are used herein.

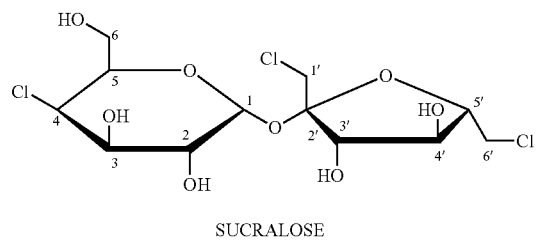

SUCRALOSE

Feed mixture, feed material, or feed stream, refers to a mixture comprising DMF and HCl. The method according to the present invention affords a purified dimethylformamide from a feed mixture. Purified dimethylformamide, or purified DMF, refers to DMF which contains a reduced amount of HCl compared to the feed mixture. As the method is a distillation procedure, it may be that the purified DMF is also lower in other contaminants when compared to the feed mixture. Also, it may be that the purified DMF which is obtained is suitable for reuse as a solvent without any further purification. However, as the invention is directed to obtaining DMF which contains a reduced amount of HCl, 'purified dimethylformamide' primarily refers to DMF which contains a reduced amount of HCl compared to the feed mixture.

DMA refers to dimethylamine. DMA may be present in a feed mixture according to the present invention because of the decomposition of DMF as described in, for example, U.S. Pat. No. 8,530,643.

When the feed mixture is distilled, a more volatile fraction and a less volatile fraction can be obtained. 'More volatile fraction' refers to a portion of the mixture which boils at a lower temperature and, when the mixture is subjected to distillation, will form an overhead vapour which can be collected, and optionally condensed to a liquid. 'Less volatile fraction' refers to a portion of a mixture which boils at a higher temperature and, when the mixture is subjected to distillation, can be collected at a lower point in the distillation column, or collected as the bottoms of the distillation process in liquid form. This less volatile fraction distils at a higher temperature than the more volatile fraction.

Other fractions may be produced in the distillation process in addition to the more volatile fraction and less volatile fraction as defined herein.

'Purified dimethylformamide product', or 'purified DMF product', refers to the portion of the collected more volatile fraction which is taken forward as product from the distillation system.

Surprisingly, it has been found that if a mixture of DMF and HCl is distilled, DMF which is substantially free of HCl can be obtained as a more volatile fraction.

Without wishing to be bound by any particular theory, a mixture containing DMF and HCl may contain species in which chloride is bound to DMF in the form of a complex. Such a complex may exhibit a boiling point which is different from uncomplexed DMF.

Depending on the concentration of HCl in DMF, it has been postulated that complexes of different $(DMF)_x.(HCl)_y$ stoichiometries may form (Maiorov et al., *Russ. Chem. Bull.*, 1993, 42, 1511-1516). In DMF and HCl mixtures of concentrations as contemplated here, it is possible that complexes with stoichiometries of $(DMF)_2.(HCl)$, and to a lesser extent (DMF).(HCl), are formed.

According to the results disclosed herein, such complexes have a higher boiling point than uncomplexed DMF. As such, a mixture containing complexed and uncomplexed DMF could be heated to a temperature sufficient to distill DMF from the mixture as a more volatile fraction, whilst the complexed DMF is retained in the liquid phase as a less volatile fraction.

The distillation may be carried out in a distillation column. Any suitable type of distillation column known to the skilled person may be used. In some embodiments, the distillation column may consist of a rectifying and a stripping section: the rectifying section the upper section; the stripping section is the lower section. In one embodiment, the feed mixture is introduced to the middle of the distillation column, between the rectifying and stripping sections.

Any internal for the distillation column known in the art may be used, including, but not limited to, trays, packings or a combination thereof. Preferably, the distillation column is a packed column. A packed column may offer the advantage of a lower pressure drop across the column when compared to a column containing trays. Packed columns contain beds of packing material which are used to bring the rising vapours into intimate contact with falling liquid in the tower. The distillation column may be packed in any suitable way known in the art. By way of example, the packing method could be, but is not limited to, random packing, structured packing or grid packing. The packing material can be any appropriate packing material known in the art. By way of example, the packing material could be one or more of, but is not limited to, spiral prismatic packing (SPP), Raschig rings, Lessing rings, Heli-Pak (wire around twisted rectangular rod), ceramic or plastic berl saddles, solid glass balls, polytetrafluoroethylene (PTFE) balls or wire mesh.

The invention can be carried out in a batch or continuous manner. A batch process may involve introducing a batch of the feed mixture to the distillation column and distilling the mixture into its components, before the distillation column is again charged with more feed mixture and the process repeated. However, it may be preferable to apply the invention in a continuous method, in which a feed mixture is continuously (without interruption) introduced to the distillation column, and separated fractions are removed continuously as output streams, such that eventually the system will be at a steady state (total output=total input).

In some embodiments, techniques may be employed to increase the efficiency of the distillation column. Any appropriate technique known in the art may be used. In one embodiment, a reflux stream may be used. As will be apparent to the skilled person, a reflux stream refers to a portion of the collected more volatile fraction that is returned to the distillation column. In one embodiment, the reflux stream may be introduced to the distillation column at a point above the point at which the feed mixture is introduced to the column. It may be preferable for the reflux stream to be introduced to the top of the distillation column. If the distillation column comprises a rectifying section, it may be preferable to introduce the reflux stream to the top of the rectifying section. Without being bound by any particular theory, it is believed that inside the column, the downflowing reflux liquid may serve to cool and condense a portion of the upflowing vapours, thereby increasing the efficiency of the distillation column.

Figure 2:
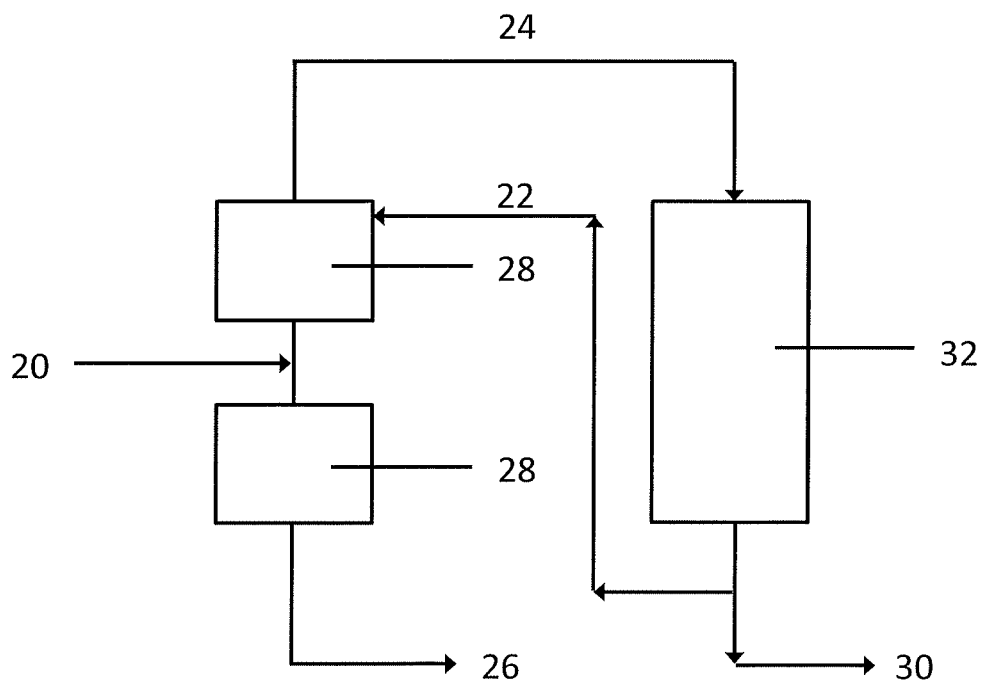
FIG. 2 is a flow diagram showing the method of the invention, in which the feed mixture is distilled in order to recover purified DMF from a mixture containing DMF and HCl.

Reflux ratio refers to the ratio between the amount of collected more volatile fraction which is returned to the distillation column as a reflux stream, and the amount of collected more volatile fraction which is taken forward as purified DMF product. With reference to FIG. 2 and the numbers used therein, the reflux ratio can be illustrated as (30):(22).

An appropriate reflux ratio can be determined by the skilled person in the art according to the operating requirements of the process and the equipment used. In one embodiment, the reflux ratio may be from 0.1:1 to 4:1 (w/w), or from 0.2:1 to 1.5:1, or from 0.2:1 to 1:1 (w/w).

If exposed to high temperatures, DMF may decompose. In one embodiment of the invention, in order to minimise decomposition of the DMF when boiled at high temperatures, it may be preferable to distil the feed mixture into the more volatile fraction and the less volatile fraction under reduced pressure, typically from 1 mbar to 1014 mbar, or from 1 mbar to 100 mbar, or from 30 mbar to 80 mbar. The distillation may be carried out at a temperature lower than the boiling point of DMF at atmospheric pressure, the temperature within the distillation vessel being typically from 0° C. to 150° C., or from 0° C. to 100° C., or from 10° C. to 85° C. In a particularly preferred embodiment, the distillation may be carried out under reduced pressure and at a temperature lower than the boiling point of DMF at atmospheric pressure.

The purified DMF has a lower chloride content than the feed mixture. The chloride content of the purified DMF may be from 0 to 1000 ppm, or 0 to 500 ppm, or from 0 to 250 ppm.

The feed mixture may have any chloride content, and may typically be from 0.1% to 10% (w/w), or from 0.5% to 5% (w/w), or from 2% to 4% (w/w).

The feed mixture can be any composition which comprises DMF and HCl, and can derive from any source. It may be that the feed mixture is derived from a reaction mixture. In some embodiments, this reaction mixture may comprise DMF, HCl, and reactants, reaction products, or a mixture of reactants and reaction products.

The feed mixture can be distilled from the reaction mixture in any appropriate method known in the art. In order to minimise the degradation of DMF when exposed to high temperatures, the distillation of the feed mixture from the reaction mixture may be conducted under reduced pressure, typically from 1 mbar to 300 mbar, or from 1 mbar to 150 mbar, or from 40 mbar to 100 mbar. The distillation of the feed mixture from the reaction mixture may be carried out at an internal temperature of from 40° C. to 150° C., or from 50° C. to 90° C. Preferably, the distillation of the feed material from the reaction mixture is carried out under reduced pressure and at a reduced temperature.

If desired, the feed mixture may be obtained directly from a reaction mixture by distillation. The reaction mixture can derive from any process. According to one embodiment, the reaction mixture may derive from a step in the synthesis of sucralose. Furthermore, the reaction mixture may be derived from a chlorination reaction of a sucrose-6-acylate to afford a sucralose-6-acylate. The feed mixture can be obtained according to procedures described in U.S. Pat. No. 8,530,643, the disclosure of which is incorporated herein by reference in its entirety, or any other appropriate method known to those skilled in the art. The reaction mixture may be distilled to afford the feed mixture and a reaction mixture bottoms stream.

The feed mixture can be obtained by distillation in a batch or continuous manner. In a batch manner, the distillation may be carried out over a time period of from 1 hour to 24 hours. The temperature, pressure, and time required are interrelated, and optimum conditions can be determined by the person skilled in the art according to the operating requirements of the process and the equipment used. In general, the removal is carried out as rapidly as possible. If longer time periods are used for the removal, then lower temperatures will generally be used, in order to minimise carbohydrate degradation.

In one embodiment, the distillation of the reaction mixture is carried out before the reaction mixture is quenched. In a further embodiment, the reaction mixture may be non-aqueous.

Following distillation of the feed mixture, a portion of the less volatile fraction may be collected. In one embodiment, the collected less volatile fraction is acidic and may be treated with a base, and filtered if necessary, to remove HCl.

Suitable bases may be hydroxides and carbonates of alkali and alkali earth metals, such as sodium hydroxide, potassium hydroxide, calcium hydroxide sodium carbonate, potassium carbonate, and calcium carbonate. Ammonia can also be used. Other bases known to the skilled person may also be used for neutralisation. The base can be an anhydrous base or an aqueous solution or suspension of the base.

In another embodiment, the reaction mixture bottoms stream (e.g. a mixture resulting from the chlorination of a sucrose-6-acylate to a sucralose-6-acylate) is collected. The reaction mixture bottoms stream may be quenched, for example, with a base. In a further embodiment, the collected less volatile fraction can be mixed with the reaction mixture bottoms stream, and the resulting mixture subsequently treated with base to quench the reaction and neutralise HCl.

A number of different bases may be used in the quenching. Bases that can be employed for quenching include alkali metal or alkaline metal hydroxides, or ammonium hydroxide. As alkali metal hydroxides, sodium and potassium hydroxide are particularly suitable. As an alkaline earth metal hydroxide, calcium hydroxide is particularly suitable. The most usual base for quenching is sodium hydroxide, due to its ready availability and low cost. Other bases known to the skilled person may also be used for quenching. The quench may be performed with an aqueous solution of the base. The aqueous solution may contain from about 5 wt % to about 50 wt %, typically from about 8 wt % to about 40 wt % of the base. Within these ranges, the solution of the base can be either "concentrated" or "dilute". If the solution of the base is concentrated, then precipitation of salts is envisaged, and in this case suitable concentrations are from 13 to 50%, or from 25 to 45% or about 35%. If the solution of the base is dilute, precipitation of salts is not envisaged, and in that case suitable concentrations are from 5 to 15%, or from 8 to 13%, or from 10 to 11%.

During the quenching, the pH of the mixture may be controlled. If the reaction mixture derives from the chlorination of a sucrose-6-acylate to a sucralose-6-acylate, the reaction mixture bottoms stream (optionally combined with the collected less volatile fraction) may be quenched to provide a sucralose-6-acylate and the acid salt of the base. In this case, the pH of the mixture may be controlled, since it may be desired that deacylation should be minimised while quenching takes place. This pH control is readily achievable by controlling the addition rate of the aqueous solution of the base while monitoring the pH within the mixture. Any method of pH-controlled addition known to the skilled person may be used.

Suitably, the pH of the mixture is maintained in the range of from about 7.5 to about 10.5 during the quenching, or from about 8.5 to about 10.5, or from about 9.5 to about 10, or from about 9.5 to about 9.75. The pH may also be maintained at a lower level, for example about 4.5, during the addition, and then raised to the desired pH when all of the base has been added. If deacylation is to be carried out as a separate step, though, a pH of more than about 10 should generally be avoided during quenching, since deacylation may then occur. In order to avoid local extremes of pH, the mixture should be adequately mixed throughout the quenching procedure.

The temperature of the reaction mixture bottoms stream during quenching may suitably be maintained in the range of from above 0° C. to about 80° C., for example, in the range of from 10° C. to 60° C., with a range of from about 12° C. to about 35° C. being typical.

In another embodiment, the neutralisation of the collected less volatile fraction, or the quench of the reaction mixture bottoms stream, or the quench and neutralisation of the mixture of the collected less volatile fraction and reaction mixture bottoms stream, may be conducted by the "dual stream quench" method, which is described in U.S. Pat. Nos. 5,530,106 and 5,498,709. In the dual stream process, the quenching conditions are attained by slow addition of the aqueous base with simultaneous slow addition of the bottoms stream into a vessel. The reaction vessel can contain an initial charge of aqueous solution of DMF. Slow addition of aqueous base and the bottoms stream allows both the pH and the temperature to be controlled during addition. The bottoms stream and aqueous base are simultaneously added slowly until the desired quantity of the bottoms stream has been added. Further aqueous base is added until the desired pH is reached. Then the temperature and pH are maintained at the desired levels for the remainder of the reaction. Generally, the pH should not be permitted to rise above about 10.5 during the course of the quenching reaction.

Quenching may alternatively be carried out by a circulated process. In the circulated process, the quenching conditions are attained by circulating the bottoms stream through a circulation loop. Bottoms stream and aqueous base are added slowly into this circulation loop. Slow addition of aqueous base and the bottoms stream allows both the pH and the temperature to be controlled during addition. Sufficient aqueous base is added until the desired pH is reached. Then the temperature and pH are maintained at the desired levels for the remainder of the reaction. This process may be run in a batch or continuous mode. Generally, the pH should not be permitted to rise above about 10.5 during the course of the quenching reaction.

Following quenching, the mixture may be neutralised by the addition of aqueous acid, for example aqueous hydrochloric acid. If the reaction mixture derives from the chlorination of a sucrose-6-acylate to a sucralose-6-acylate, the sucralose-6-acylate can then be isolated by conventional means, if desired, or deacylation can be carried out without isolation of the sucralose-6-acylate.

Obtaining the Reaction Mixture

The reaction mixture can derive from any process. According to one embodiment, the reaction mixture may derive from a step in the synthesis of sucralose. Furthermore, the reaction mixture may be derived from a chlorination reaction of a sucrose-6-acylate to afford a sucralose-6-acylate.

In one such embodiment, the chlorination reaction can be carried out by a number of methods, such as those disclosed in EP 0043649, EP 0409549, US 2006/0205936, and US 2007/0100139.

A number of chlorinating agents may be used in the present invention in order to chlorinate the 4, 1' and 6' positions of the sucrose-6-acylate. Suitable examples include those selected from the group consisting of phosgene, Arnold's reagent (also known as (chloromethylene)dimethyliminium chloride or as (chloromethylene)dimethylammonium chloride), phosphorous oxychloride, phosphorous pentachloride, thionyl chloride, oxalyl chloride, methanesulfonyl chloride, sulfuryl chloride, diphosgene (trichloromethyl chloroformate) and triphosgene (bis(trichloromethyl)carbonate). Other suitable chlorinating agents known to the skilled person may also be used. Preferably, the chlorinating agent is phosgene or Arnold's reagent.

The chlorinating agent is preferably added in excess with respect to the sucrose-6-acylate, and preferably in large excess. At least three molar equivalents of chlorinating agent are required per mole of sucrose-6-acylate in order to chlorinate the 4, 1' and 6' positions; thus, an excess amount of chlorinating is any amount above three molar equivalents per mole. In a preferred embodiment, the chlorinating agent is added in an amount of at least seven molar equivalents per mole of the sucrose-6-acylate. Typically, the molar ratio of the chlorinating agent to the sucralose-6-acylate is about 7:1 to about 11:1.

A number of reaction conditions can be used to achieve the chlorination according to the present invention. U.S. Pat. No. 4,980,463, the disclosure of which is incorporated herein by reference, for example, discloses a two stage process in which chlorination is carried out at two different temperatures, a temperature not higher than about 85° C. and a temperature of at least about 100° C. but not higher than about 130° C. to effect chlorination. US 2007/0100139, the disclosure of which is incorporated herein by reference, discloses a process in which the reaction mixture is heated between 75° C. to 100° C. to effect chlorination.

In general, the reaction temperature for the chlorination reaction according to the present invention is typically from 85° C. to 130° C.

The reaction time for the chlorination according to the present invention depends on the temperature employed, with lower temperatures requiring longer reaction times. The skilled person can easily determine the optimum reaction time for a given reaction temperature by monitoring the reaction. If the reaction time is too short, insufficient conversion to the 4,1',6'-trichloro-4,1',6'-trideoxy-galactosucrose-6-acylate occurs. If the reaction time is too long, over-chlorination will occur, resulting in increased levels of tetra-chlorinated by-products.

Post-Quench Treatment of the Reaction Mixture Bottoms Stream

The present invention also extends to a method of producing sucralose by deacylating at least a portion of the 4,1',6'-trichloro-4,1',6'-trideoxy-galactosucrose-6-acylate to form the sucralose. The deacylation can be performed before or after the removal of the remaining DMF from the reaction mixture bottoms stream, but is preferably performed before the removal of the remaining DMF. After quenching, or in a combined process with the quenching, at least a portion of the 4,1',6'-trichloro-4,1',6'-trideoxy-galactosucrose-6-acylate can be deacylated to afford sucralose.

The deacylation can be carried out, for example, by the method disclosed in U.S. Pat. No. 6,890,581, incorporated herein in its entirety by reference. Other methods for deacylating sucralose-6-acylates, and for isolating and/or purifying sucralose, are disclosed in U.S. Pat. Nos. 5,977,349, 6,943,248, 6,998,480, 7,049,435, 6,809,198, 6,646,121, 5,298,611, 5,498,709, US2006/0188629, US2006/0276639, US2007/0015916, US2007/0160732, and US2007/0270583, the disclosures of which are all incorporated herein by reference.

The deacylation can be carried out by treatment with a base. Any suitable base may be used, and suitable bases are those already mentioned as the base for quenching. For convenience, it is preferred to use the same base for deacylation and quenching. It is particularly preferred to use sodium hydroxide as the base in both cases.

In order to effect deacylation, it is necessary to raise the pH of the mixture, typically to a level above that at which the quenching was carried out. In order to minimise decomposition of the DMF (if the deacylation is performed before the removal of remaining DMF), the deacylation is preferably carried out under carefully controlled conditions. Therefore, the deacylation is preferably performed at a pH of from 10 to 13.5, more preferably from 10 to 12, and most preferably from 10.5 to 11.2, at a temperature of from 60 to 0° C., more preferably from 40 to 0° C., and most preferably from 35° C. to 25° C., the higher pH being used with the lower temperature and vice versa.

If the deacylation is carried out after the removal of remaining DMF, then the deacylation conditions are less critical, although the above described conditions can still be used. In general, the deacylation may be carried out at a pH of from 8 to 14 and a temperature of from 0 to 60° C., or at a pH of from 10 to 12 and a temperature of from 0 to 40° C.

The deacylation reaction can be conveniently monitored by HPLC. For optimum yields, it is important to monitor the progress of the deacylation reaction, and neutralise the mixture when the reaction is complete. The pH of the mixture should be adjusted to from 6 to 8.5, or approximately 7.5. The mixture can conveniently be neutralised using aqueous hydrochloric acid, or using citric acid or acetic acid. Alternatively, the mixture can be neutralised with gaseous carbon dioxide.

The quenching and deacylation can be carried out in a batch or continuous manner and may be carried out in a single vessel or in multiple vessels. Equally, a combination transitioning between continuous and batch from one or more vessels to one or more vessels can be used. The choice of arrangement will be dictated by practical considerations.

Although quenching and deacylation are carried out sequentially in embodiments described above, it is also possible for quenching and deacylation to be carried out together. In this embodiment, the aqueous solution of a base is added to the reaction mixture bottoms stream exactly as described above for quenching, but with the exception that the pH of the stream is allowed to rise immediately to a level where deacylation can occur, rather than being controlled to minimise deacylation. Suitable pH conditions for effecting deacylation are discussed above, and are equally applicable here.

The removal of remaining DMF can be carried out by means known in the art, such as distillation, distillation under reduced pressure, steam distillation, steam stripping, or by use of an agitated thin film drier or spray drier. It is preferred that the removal of the DMF is carried out by steam stripping. Such steam stripping can be carried out as described in EP 0708110. Typically, at least 90% of the DMF present in the mixture at the end of deacylation (if the removal of the remaining DMF is carried out after deacylation), or after the quench of the chlorination reaction, (if the removal of the remaining DMF is carried out before the deacylation) is removed during this step. More typically, at least 99% is removed.

Obtaining the Feed Material

One embodiment of a method according to the present invention is shown in FIGS. 1 and 2. Referring to FIG. 1, following the chlorination of a sucrose-6-acylate to a sucralose-6-acylate, a non-aqueous and unquenched reaction mixture stream (10) is obtained, which contains carbohydrates, DMF, and HCl.

The chloride content may be determined by titration with silver nitrate solution, or by Ion Chromatography.

The feed material is obtained from a reaction mixture as demonstrated by U.S. Pat. No. 8,530,643. In this invention, the unquenched reaction mixture stream (10) is concentrated in a vessel (16) while heating at from 40° C. to 150° C., preferably from 50° C. to 90° C., and most preferably at 75° C., under a reduced pressure of from 1 mbar to 300 mbar, preferably from 1 and 150 mbar, more preferably from 40 mbar to 100 mbar, and most preferably at 60 mbar to between 60-70% by mass with overhead vapour containing both DMF and HCl. This vapour is condensed by cooling, and the liquid mixture is collected in vessel (18). The collected liquid stream in vessel (18) is hereafter called the "feed mixture" (20). Depending on the composition of the reaction mixture stream (10), the concentration of the reaction mixture stream (10) by weight, and concentration conditions (temperature and pressure), the composition of overhead vapour stream (12) may change during this concentration procedure. The composition of the final condensed liquid in vessel (18) may vary in chloride level from 0.1% to 10%, or from 0.5% to 5%, or from 2% to 4%. Depending on the process, either the overhead vapour stream (12) may be taken further to the next step in the process without condensing in vessel (18) and thus essentially stream (12) is feed mixture (20) in a vapour phase, or as described in Examples 3 to 12, it can be feed mixture (20) and be used in a liquid phase. In both vapour stream (12) and condensed stream in vessel (18), DMF is the major component and HCl is the minor component, with chloride levels measured as from 0.1% to 10%, or from 0.5% to 5%, or from 2% to 4%.

Purification and Recovery of DMF from the Feed Material

Referring to FIG. 2, after obtaining the feed stream (20), which contains DMF as the major component and HCl as the minor component, HCl is concentrated at the bottom of a packed distillation column (28) and the concentrate is transferred out of column (28) as a bottoms stream (26). Purified DMF is obtained in vessel (32). The distillation column (28) can consist of two sections which are: a rectifying section at the top of the column (28), which is packed, and a stripping section at the bottom of the column (28), which is packed. The feed stream (20) may be introduced to the centre of the column (28), between the rectifying and stripping sections (28). The column (28) operates at reduced pressures and reduced temperatures. The vessel is preferably at a temperature of from 0° C. and 150° C., more preferably from 0° C. and 100° C., and even more preferably from 10° C. to 85° C. The vessel is under reduced pressure of from 1 mbar to 1014 mbar, preferably from 1 mbar to 100 mbar, and more preferably from 30 mbar to 80 mbar. A reboiler is used to heat the feed stream (20), and to boil the liquid in the distillation column (28). The vapour-liquid phase separation in column (28) may be accomplished using a specific packing with high surface area. Then, the overhead (vapour) stream (24) is condensed by cooling. This may be achieved by glycol cooling. The condensed liquid is collected in vessel (32). The collected liquid in vessel (32) could be further purified by transferring a portion back to the column (28) as reflux stream (22), while recovered DMF with low HCl content is transferred out of vessel (32) as purified DMF product (30). The reflux stream (22) may be transferred to the column (28) at a point above the point at which the feed mixture is introduced to the distillation column. Preferably, the reflux stream (22) is transferred to the distillation column at the top of the rectifying section (28). In an embodiment relevant to sucralose synthesis, the bottoms stream (26) may be mixed with the reaction mixture bottoms stream (14) to be further quenched by the dual stream quench method at pH 9.5 and 32° C. using 11% NaOH.

EXAMPLES

The reaction mixture is derived from a chlorination reaction of sucrose-6-acetate to afford sucralose-6-acetate. Such a mixture can be obtained, for example, by the methods disclosed in U.S. Pat. No. 8,530,643, as described below.

The mixture which undergoes chlorination to afford sucralose-6-acetate comes from the acetylation of sucrose. This mixture is produced, for example, by the methods disclosed in U.S. Pat. No. 5,470,969. A typical composition of this mixture is as follows:

TABLE 1

| Description | % of total, w/w |
|---|---|
| Sucrose-6-acetate | 29.4 |
| Other carbohydrates | 10.4 |
| DMF | 52.7 |
| Others | 7.5 |

The chlorination of sucrose-6-acetate is conducted as follows:
1. 25 g of Arnold's reagent is charged to a 250 mL round bottom flask equipped with a stirrer bar.
2. Approximately 50 g of DMF is added to the flask.
3. The slurry is cooled to 0-5° C.
4. 20 grams of carbohydrate feed is added dropwise at temperature <20° C.
5. After addition is complete, the mixture is stirred at room temperature for 3-4 hours followed by heating at 100° C. for 11 hours. This affords the "reaction mixture". A typical composition of the reaction mixture is as follows:

TABLE 2

| Description | % of total, w/w |
|---|---|
| Carbohydrates | 10.0 |
| DMF | 34.2 |
| $(DMF)_2 \cdot HCl$ | 37.5 |
| $DMA \cdot HCl$ | 12.3 |
| Other | 6.3 |

The $(DMF)_2.HCl$ and $DMA.HCl$ complexes correspond to the reaction mixture having a total calculated chloride content of 12.6% (w/w).

Examples 1 and 2 exemplify methods of obtaining the feed material from a reaction mixture with the above composition.

Example 1

Referring to FIG. 1, 1088 kg of unquenched reaction mixture (10) as described in Table 2 was transferred into a fully jacketed vessel (16) equipped with an overhead mechanical stirrer, a recirculation pump, an exchanger, a vacuum pump, a condenser, an overhead collection vessel (18) and a NaOH scrubber. Then, the reaction mixture stream (10) was concentrated in vessel (16) while heating at 72° C. at 60 mbar to 74.5% by mass. The overhead vapours (12) were condensed at 0° C. using glycol cooling and were collected in vessel (18) as a liquid phase. Here, the liquid in vessel (18) is the feed mixture which is used for the next step in the method. Samples were assayed and the feed mixture collected in vessel (18) gave 1.9% chloride as the major impurity, with the remainder of DMF. A sample of the residue in vessel (16) was assayed giving 16.3% chloride. The reaction mixture bottoms stream (14) was quenched by the dual stream quench method at pH 9.5 and 32° C. using 11% NaOH. Alternatively, prior to the quench of the reaction mixture bottoms stream (14) it may be mixed with stream (26) and then quenched.

Example 2

1200 kg of unquenched reaction mixture (10) as described in Table 2 containing 12.6% chloride was transferred into a fully jacketed vessel (16) equipped with an overhead mechanical stirrer, a recirculation pump, an exchanger, a vacuum pump, a condenser, an overhead collection vessel (18) and a NaOH scrubber. Then, the reaction mixture stream (10) was concentrated in vessel (16) while heating at 84-87° C. at 90-110 mbar to 66% by mass. The overhead vapours (12) were condensed at 5° C. using glycol cooling and were collected in vessel (18) as a liquid phase. Here, the liquid in vessel (18) is the feed mixture which is used for the next step in the method. Samples were assayed and the feed mixture collected in vessel (18) gave 2.2% chloride as the major impurity with the remainder of DMF. A sample of the residue in vessel (16) was assayed giving 18.0% chloride. The reaction mixture bottoms stream (14) was quenched by the dual stream quench method at pH 9.5 and 32° C. using 11% NaOH. Alternatively, prior to the quench of the reaction mixture bottoms stream (14) it may be mixed with stream (26) and then quenched.

Examples 3 to 12 exemplify methods of obtaining purified DMF from a feed material obtained according to Examples 1 and 2. The data obtained from these examples are presented in Tables 3 to 5.

Example 3

Referring to FIG. 2, and referring to the feed mixture prepared according to Examples 1 and 2, a feed mixture stream (20) with 1.7% chloride with the remainder DMF was preheated to 57° C. while transferred continuously to a packed column (28) at a flow rate of 5.9 kg/h. This packed distillation column (28) operated at 50 mbar and the liquid inside was heated by a reboiler to generate sufficient boiling of the liquid at 72° C. to generate overhead stream (24) with a temperature of 65° C. at the top of the column as a vapour phase. This overhead stream (24) as vapour was condensed at 5° C. using glycol cooling and the obtained liquid phase with a temperature of about 20° C. was collected in vessel (32). Then, simultaneously and continuously, the liquid overhead stream from vessel (32) was transferred back to the column as reflux stream (22) at a rate of 4.5 kg/h and at the same time transferred as purified DMF product (30) to be collected in a container at a rate of 4.4 kg/h. At the steady state, the reflux ratio (which is the ratio between reflux stream (22) flow rate and purified DMF product (30) flow rate) was 1:1. The more volatile fraction from the vessel (32) taken forward as purified DMF product (30) was tested showing 71 ppm chloride with DMF as remainder. This purified DMF is practical for reuse in many solvent applications. The low levels of chloride mean that the DMF may be tolerable for subsequent use without further purification. In an embodiment relevant to sucralose synthesis, the purified DMF has a suitably low chloride content for the DMF to be used as the solvent in the chlorination reaction of a sucrose-6-acylate to afford a sucralose-6-acylate. The DMF recovery was calculated to be 75%. Also, at the steady state the bottoms stream (26), which is a concentrated chloride stream, was discharged from vessel (28) at a rate of 1.5 kg/h to purge out chloride. Analysis of the bottoms stream (26) showed 9.6% chloride. The bottoms stream (26), which is a residue, can be mixed with the reaction mixture bottoms stream (14) to quench by the "dual stream quench" method at pH 9.5 and 32° C. using 11% NaOH. Data from this example are given in Tables 3 to 5.

Example 4

Referring to FIG. 2, and referring to the feed mixture prepared according to Examples 1 and 2, a feed mixture stream (20) with 2.1% chloride with the remainder DMF was preheated to 68° C. while transferred continuously to a packed column (28) at a flow rate of 5.2 kg/h. This packed distillation column (28) operated at 51 mbar and the liquid inside was heated by a reboiler to generate sufficient boiling of the liquid at 73° C. to generate overhead stream (24) with a temperature of 64° C. at the top of the column as a vapour phase. This overhead stream (24) as vapour was condensed at 5° C. using glycol cooling and the obtained liquid phase with a temperature of about 20° C. was collected in vessel (32). Then, simultaneously and continuously the liquid overhead stream from vessel (32) was transferred back to the column as reflux stream (22) at a rate of 4.8 kg/h and at the same time transferred as purified DMF product (30) to be collected in a container at a rate of 5.2 kg/h. At the steady state the reflux ratio (which is the ratio between reflux stream (22) flow rate and purified DMF product (30) flow rate) was 0.9:1. The more volatile fraction from the vessel (32) taken forward as purified DMF product (30) was tested showing 44 ppm chloride with DMF as remainder. This purified DMF is practical for reuse in many solvent applications. The low levels of chloride mean that the DMF may be tolerable for subsequent use without further purification. In an embodiment relevant to sucralose synthesis, the purified DMF has a suitably low chloride content for the DMF to be used as the solvent in the chlorination reaction of a sucrose-6-acylate to afford a sucralose-6-acylate. The DMF recovery was calculated to be 77%. Also, at the steady state the bottoms stream (26), which is a concentrated chloride stream, was discharged from vessel (28) at a rate of 1.2 kg/h to purge out chloride. Analysis of the bottoms stream (26) showed 11.9% chloride. The bottoms stream (26), which is a residue, can be mixed with the reaction mixture bottoms stream (14) to quench by the dual stream quench method at pH 9.5 and 32° C. using 11% NaOH. Data from this example are given in Tables 3 to 5.

Examples 5 to 9

Using the method set out above in Example 4, a feed stream (20) with 2.1% chloride with the remainder DMF was distilled to give purified DMF product with low levels of chloride between 32 and 126 ppm, with DMF recovery calculated to be between 74%-89%. The reflux ratios of these examples, and the data generated, are given in Tables 3 to 5.

Example 10

Referring to FIG. 2, and referring to the feed mixture prepared according to Examples 1 and 2, a feed mixture stream (20) with 2.2% chloride with the remainder DMF was preheated to 66° C. while transferred continuously to a packed column (28) at a flow rate of 8.1 kg/h. This packed distillation column (28) operated at 50 mbar and the liquid inside was heated by a reboiler to generate sufficient boiling of the liquid at 71° C. to generate overhead stream (24) with a temperature of 66° C. at the top of the column as a vapour phase. This overhead stream (24) as vapour was condensed at 5° C. using glycol cooling and the obtained liquid phase with a temperature of about 20° C. was collected in vessel (32). Then, simultaneously and continuously the liquid overhead stream from vessel (32) was transferred back to the column as reflux stream (22) at a rate of 2.8 kg/h and at the same time transferred as purified DMF product (30) to be collected in a container at a rate of 7.1 kg/h. At the steady state the reflux ratio, which is the ratio between reflux stream (22) flow rate and purified DMF product (30) flow rate, was 0.4:1. The more volatile fraction from the vessel (32) taken forward as purified DMF product (30) was tested showing 71 ppm chloride with DMF as remainder. This purified DMF is practical for reuse in many solvent applications. The low levels of chloride mean that the DMF may be tolerable for subsequent use without further purification. In an embodiment relevant to sucralose synthesis, the purified DMF has a suitably low chloride content for the DMF to be used as the solvent in the chlorination reaction of a sucrose-6-acylate to afford a sucralose-6-acylate. The DMF recovery was calculated to be 86%. Also, at the steady state the bottoms stream (26), which is a concentrated chloride stream, was discharged from vessel (28) at a rate of 1.1 kg/h to purge out chloride. Analysis of the bottoms stream (26) showed 13.8% chloride. The bottoms stream (26), which is a residue, can be mixed with the reaction mixture bottoms stream (14) to quench by the dual stream quench method at pH 9.5 and 32° C. using 11% NaOH. Data from these examples are given in Tables 3 to 5.

Examples 11 to 12

Using the method set out above in Example 10, a feed stream (20) with 2.2% chloride with the remainder DMF was distilled to give purified DMF product with low levels of chloride between 59 and 100 ppm, with DMF recovery calculated to be between 80%-89%. Reflux ratios of these examples, and the data generated, are given in Tables 3 to 5.

Emboldened numbers used in Tables 2 to 4 refer to the corresponding numbers in FIGS. 1 and 2.

TABLE 3

| Example # | Feed (20) kg/h | Reflux (22) kg/h | Bottoms (26) kg/h | Purified DMF (30) kg/h | Reflux ratio (22:30) | DMF recovery $\left(\frac{30}{30+26} \times 100\%\right)$ (wt. %) |
|---|---|---|---|---|---|---|
| 3 | 5.9 | 4.5 | 1.5 | 4.4 | 1.0:1 | 75 |
| 4 | 5.2 | 4.8 | 1.2 | 5.2 | 0.9:1 | 81 |
| 5 | 5.7 | 3.6 | 1.4 | 4.4 | 0.8:1 | 76 |
| 6 | 5.7 | 2.7 | 1.5 | 4.5 | 0.6:1 | 75 |
| 7 | 5.7 | 4.0 | 1.1 | 5.2 | 0.8:1 | 83 |
| 8 | 8.2 | 5.6 | 1.1 | 6.8 | 0.8:1 | 86 |
| 9 | 8.0 | 4.1 | 0.9 | 6.9 | 0.6:1 | 88 |
| 10 | 8.1 | 2.8 | 1.1 | 7.1 | 0.4:1 | 87 |
| 11 | 10.0 | 3.7 | 1.1 | 8.7 | 0.4:1 | 89 |
| 12 | 10.0 | 3.3 | 2.0 | 8.0 | 0.4:1 | 80 |

TABLE 4

| Example # | Feed (20) Temperature ° C. | Overhead (24) Temperature ° C. | Bottoms (26) Temperature ° C. | Vessel (28) Pressure mbar |
|---|---|---|---|---|
| 3 | 57 | 65 | 72 | 50 |
| 4 | 68 | 64 | 73 | 51 |
| 5 | 59 | 65 | 71 | 50 |
| 6 | 63 | 65 | 71 | 50 |
| 7 | 63 | 65 | 74 | 51 |
| 8 | 65 | 65 | 75 | 51 |
| 9 | 67 | 64 | 74 | 50 |
| 10 | 66 | 66 | 71 | 50 |
| 11 | 64 | 65 | 75 | 50 |
| 12 | 60 | 65 | 73 | 50 |

TABLE 5

| Example # | Feed (20) Chloride, (wt. %) | Bottoms (26) Chloride, (wt. %) | Purified DMF (30) Chloride, ppm |
|---|---|---|---|
| 3 | 1.7 | 9.6 | 71 |
| 4 | 2.1 | 11.9 | 44 |
| 5 | 2.1 | 8.8 | 36 |
| 6 | 2.1 | 7.5 | 36 |
| 7 | 2.1 | 11.2 | 126 |
| 8 | 2.1 | 13.8 | 30 |
| 9 | 2.1 | 16.5 | 32 |
| 10 | 2.2 | 13.8 | 255 |
| 11 | 2.2 | 18.5 | 100 |
| 12 | 2.2 | 11.2 | 59 |

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:
1. A method of producing purified dimethylformamide from a feed mixture comprising dimethylformamide and hydrogen chloride, comprising:
distilling the feed mixture to afford a more volatile fraction and a less volatile fraction, wherein the more volatile fraction is lower in hydrogen chloride, measured as chloride, than the less volatile fraction, and collecting the more volatile fraction to afford a collected more volatile fraction, at least a portion of which affords a purified dimethylformamide product that is lower in hydrogen chloride, measured as chloride, than the feed mixture;

wherein the hydrogen chloride content of the feed mixture, measured as chloride, is from 0.1% to 10% (w/w) and the hydrogen chloride content of the purified dimethylformamide, measured as chloride, is from 0 to 1000 ppm.

2. The method according to claim 1 wherein the hydrogen chloride content, measured as chloride (w/w), of the purified dimethylformamide is less than 50% of the hydrogen chloride content, measured as chloride (w/w), of the feed mixture.

3. The method according to claim 1 wherein the hydrogen chloride content, measured as chloride (w/w), of the purified dimethylformamide is less than 25% of the hydrogen chloride content, measured as chloride (w/w), of the feed mixture.

4. The method according to claim 1 wherein the hydrogen chloride content, measured as chloride (w/w), of the purified dimethylformamide is less than 10% of the hydrogen chloride content, measured as chloride (w/w), of the feed mixture.

5. The method according to claim 1, wherein the distillation of the feed mixture is carried out in a distillation column.

6. The method according to claim 5, wherein the distillation column comprises an upper rectifying section and a lower stripping section.

7. The method according to claim 6, wherein the feed mixture is introduced to the distillation column between the rectifying and stripping sections thereof.

8. The method according to claim 5, wherein another portion of the collected more volatile fraction is returned to the distillation column as a reflux stream.

9. The method according to claim 8, wherein the reflux stream is introduced to the distillation column at a point above the point at which the feed mixture is introduced to the distillation column.

10. The method according to claim 8, wherein the reflux stream is introduced to the distillation column at the top of the rectifying section.

11. The method according to claim 8, wherein the ratio of the amount of the collected more volatile fraction returned as a reflux stream to the amount of the collected more volatile fraction taken forward as purified dimethylformamide product is from 0.1:1 to 4:1 (w/w).

12. The method according to claim 11, wherein the ratio of the amount of the collected more volatile fraction returned as a reflux stream to the amount of the collected more volatile fraction taken forward as purified dimethylformamide product is from 0.2:1 to 1.5:1 (w/w).

13. The method according to claim 1, wherein the feed mixture is an overhead vapor derived from a distillation of a reaction mixture, wherein the reaction mixture is derived from a a chlorination reaction of a sucrose-6-acylate to afford a sucralose-6-acylate and the reaction mixture comprises dimethylformamide, hydrogen chloride, sucralose-6-acylate, and reactants; or the reaction mixture comprises dimethylformamide, hydrogen chloride, sucralose-6-acylate, and other reaction products; or the reaction mixture comprises dimethylformamide, hydrogen chloride, reactants, sucralose-6-acylate, and other reaction products.

14. The method according to claim 13, wherein the feed mixture is distilled from the reaction mixture to further afford a reaction mixture bottoms stream.

15. The method according to claim 13, wherein the reaction mixture is non-aqueous.

16. The method according to claim 13, wherein the reaction mixture is unquenched.

17. The method according to claim 14, wherein the less volatile fraction is collected and mixed with the reaction mixture bottoms stream thereby producing a collected mixture, and
the collected mixture is added to a vessel and a base is simultaneously added to the vessel to quench the reaction mixture in the collected mixture and to neutralize the hydrogen chloride.

18. The method according to claim 1, wherein the less volatile fraction is collected and treated with a base to form a chloride salt of the base, and the chloride salt of the base is removed.

19. The method according to claim 5, wherein the pressure in the distillation column is from 1 mbar to 1014 mbar.

20. The method according to claim 19, wherein the pressure in the distillation column is from 1 mbar to 100 mbar.

21. The method according to claim 5, wherein the temperature in the distillation column is from 0° C. to 150° C.

22. The method according to claim 21, wherein the temperature in the distillation column is from 10° C. to 85° C.

23. The method according to claim 13, wherein the reaction mixture is distilled to afford the feed mixture under a pressure of from 1 mbar to 300 mbar.

24. The method according to claim 13, wherein the reaction mixture is distilled to afford the feed mixture at a temperature of from 40° C. to 150° C.

25. The method according to claim 13, wherein the chlorination reaction further comprises the step of converting at least one portion of said sucralose-6-acylate to sucralose.

26. The method according to claim 25, wherein the sucralose is isolated from the reaction mixture.

* * * * *